United States Patent
Miles

(10) Patent No.: US 12,274,690 B2
(45) Date of Patent: *Apr. 15, 2025

(54) SYSTEM AND METHOD FOR INCORPORATING CBD/THC CANNABINOID NANOPARTICLE CARRIER COMPOSITIONS INTO PARTICULATE FOODS AND FOOD ADDITIVES

(71) Applicant: Aaron Miles, McKinleyville, CA (US)

(72) Inventor: Aaron Miles, McKinleyville, CA (US)

( * ) Notice: Subject to any disclaimer, the term of this patent is extended or adjusted under 35 U.S.C. 154(b) by 815 days.

This patent is subject to a terminal disclaimer.

(21) Appl. No.: 17/302,635

(22) Filed: May 7, 2021

(65) Prior Publication Data
US 2021/0251950 A1      Aug. 19, 2021

Related U.S. Application Data

(63) Continuation-in-part of application No. 16/946,838, filed on Jul. 8, 2020, now Pat. No. 11,497,727.

(60) Provisional application No. 62/704,379, filed on May 7, 2020, provisional application No. 62/871,653, filed on Jul. 8, 2019.

(51) Int. Cl.
| | |
|---|---|
| A61K 31/05 | (2006.01) |
| A23B 2/746 | (2025.01) |
| A23B 2/771 | (2025.01) |
| A23L 27/10 | (2016.01) |
| A23L 27/40 | (2016.01) |
| A23L 33/105 | (2016.01) |
| A23P 10/22 | (2016.01) |
| A61K 9/00 | (2006.01) |
| A61K 9/16 | (2006.01) |
| A61K 31/352 | (2006.01) |

(52) U.S. Cl.
CPC ............ *A61K 31/352* (2013.01); *A23B 2/746* (2025.01); *A23B 2/771* (2025.01); *A23L 27/10* (2016.08); *A23L 27/40* (2016.08); *A23L 33/105* (2016.08); *A23P 10/22* (2016.08); *A61K 9/0056* (2013.01); *A61K 9/1617* (2013.01); *A61K 9/1694* (2013.01); *A61K 31/05* (2013.01); *A23V 2002/00* (2013.01)

(58) Field of Classification Search
CPC .................................................... A61K 31/352
See application file for complete search history.

(56) References Cited

U.S. PATENT DOCUMENTS 11,497,727 B2 * 11/2022 Miles ................... A61K 9/1075

FOREIGN PATENT DOCUMENTS

WO    WO-2018089863 A1 *  5/2018  ............ A61K 31/05

OTHER PUBLICATIONS

Feldman, Understanding 'Evergreening' : Making Minor Modifications Of Existing Medications To Extend Protections, Health Affairs Jun. 2022 41:6, 801-804.*
Dwivedi, Evergreening: A deceptive device in patent rights, Technology in Society 32 (2010) 324-330.*
G Dwivedi, 'Evergreening: A deceptive device in patent rights' (2020) Technology in Society, vol. 32, No. 4, 324-330.*

\* cited by examiner

*Primary Examiner* — Nizal S Chandrakumar
(74) *Attorney, Agent, or Firm* — Andrew F. Young, Esq.; Nolte Lackenbach Siegel

(57) ABSTRACT

A method of producing a cannabinoid nanoparticle carrier composition for administration to a human and thereafter producing a consumable food product including the cannabinoid nanoparticle emulsification. The cannabinoid nanoparticle carrier composition is combined with a particulate food product, herb or spice, sugar, salt, or particulate preservative, mixed into a slurry or suspension, dried, and then ground to a size suitable for human consumption.

15 Claims, No Drawings

SYSTEM AND METHOD FOR INCORPORATING CBD/THC CANNABINOID NANOPARTICLE CARRIER COMPOSITIONS INTO PARTICULATE FOODS AND FOOD ADDITIVES

CROSS REFERENCES TO RELATED APPLICATIONS

The present application claims the benefit of the filing date of U.S. Provisional Patent Application Ser. No. 62/704,379, filed May 7, 2020 (May 7, 2020), U.S. Provisional Patent Application Ser. No. 62/871,653, filed Jul. 8, 2019 (Jul. 8, 2019), and U.S. patent application Ser. No. 16/946,838, filed Jul. 8, 2020 (Jul. 8, 2020), which applications are incorporated in their entireties by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

BACKGROUND OF THE INVENTION

Field of the Invention: The present invention relates most generally to water soluble emulsions, more particularly to emulsions containing water-immiscible cannabinoids, still more particularly to a cannabinoid nanoparticle carrier composition suitable for therapeutic use, yet further still to a method of making dried particulate CBD/THC-containing herbs, spices, flavorings, chemical preservatives, salts, sugars, and monosodium glutamate by submerging the particles with a cannabinoid nanoparticle carrier composition to make a slurry or suspension and drying the slurry or suspension using one of several food drying methods, preferably spray drying or drum drying.

Background Discussion: Cannabinoid emulsions are known, as are lipid based cannabinoid compositions. U.S. Pat. No. 10,028,919, to Kaufman, describes one such composition. And U.S. Pat. App. Ser. No. 2009/01810890, by Kottayil, describes methods for making an effective amount of a cannabinoid in a semi-aqueous solution buffered to a pH of 5-10.

However, these two patent publications, while reflecting the current state of the art of which the present inventor is aware, do not teach or disclose, suggest, show, or otherwise render obvious, either singly or when considered in combination, the inventive method described herein. Specifically, the cited references teach cannabinoid products extremely involved manufacturing processes. The present invention, by contrast, includes as a predicate a simple method of formulating a water soluble, lipid-based cannabinoid nanoparticle carrier composition which includes the use of emulsifiers (surface active agents) and sonication or ultrasonic processes to render a cannabinoid nanoemulsion, the method described herein and in co-pending patent application Ser. No. 16/946,838, filed Jul. 8, 2020.

Cannabis oil emulsions of the kind made possible by the emulsification method described herein are known to be incorporated or used in the production of CBD- and/or THC-containing products such as topical lotions, tinctures, salves, cosmetics, skin care products, hair care products, lip balms, lozenges, foodstuffs and beverages, food supplements, medications, liquids for e-cigarettes (utility articles), tobacco substitutes, pet treats, and so on. Cannabinoids are lipophilic/hydrophobic compounds. When intended for ingestion, they must be combined with an oil to facilitate absorption in the digestive tract, and for stable emulsions they call for the use of an emulsifier. Most call for the use of lecithin or lecithin-based essential phospholipids.

BRIEF SUMMARY OF THE INVENTION

The present invention is a system and method for extracting and making cannabinoid emulsifications, as well as the product produced thereby. The present invention includes a method of incorporating such cannabinoid emulsifications in particulate foods and food additives, such as spices, flavorings, chemical preservatives, salt, sugar, and monosodium glutamate.

In its most essential aspect, the present invention is a method of producing a cannabinoid nanoparticle carrier composition for administration to a human, including the steps of: (a) mixing non-ionic surfactants with cannabinoid oils and lipids in a mixing vessel; (b) processing the mixture made in step (a) using sonication for a predetermined time at a predetermined amplification until completely processed and substantially all of the cannabinoid oils are reduced to nanoparticle size in a cannabinoid oil complex (COC); (c) dissolving an acid in a carrier fluid to make an acidic carrier fluid solution; (d) mixing the COC made in steps (a) and (b) with the acidic carrier fluid solution made in step (c); and (e) sonicating the mixture made in step (d) using an ultrasonic liquid processor operated at a predetermined amplitude for a predetermined time at a controlled temperature.

In embodiments, the foregoing method may include a first mixing step involving mixing non-ionic surfactants with cannabinoid oils and lipids in relative proportions of 5:9:9 by weight.

In further embodiments, the mixing step includes mixing approximately 5000 mg of non-ionic surfactants with approximately 9000 mg of cannabinoid oils, and approximately 9000 mg lipids.

In still further embodiments, the first sonication step includes inducing sonication for approximately 90 seconds at 60% amplification.

Still other embodiments include sonication using an ultrasonic liquid processor.

In other embodiments, step of making an acidic carrier fluid solution entails dissolving approximately 1000 mg of ascorbic acid in a carrier fluid, such as distilled water, glycerides, lipids, and mixtures thereof.

Other embodiments can include making an acidic carrier fluid solution consisting of approximately 76 g distilled water and 1000 mg ascorbic acid.

In embodiments, the second sonication step can include sonicating at 60% using ultrasonic liquid processor. This embodiment may further include sonicating at 60% amplitude, and still further it may include continuing the sonication a predetermined time, e.g., approximately 5 minutes at a constant temperature, e.g., 24 C.

Unlike most emulsifications, this composition does not include lecithin or lecithin-based essential phospholipids and relies instead on sonication or ultrasonic technology alone to force the emulsification. Once produced, the emulsification is combined with any of a number of suitable and commonly used herbs, spices, flavorings, chemical preservatives, salts, sugars, and monosodium glutamate, alone or in combination, to make a slurry or a suspension. The slurry is then evaporated or dried to a solid state using a low temperature food drying process, and preferably a spray dry or drum dry process at relatively low temperatures in the practical operating ranges, preferably lower than 200 C. Exemplary industrial equipment.

The resulting solids are ground, pulverized, milled, or comminuted to a nominal particle mass size comporting with sugar and salt quality production mesh standards, e.g., 100% pass through at 80 mesh. Machinery for the finishing step may include industrial salt crushing machines, such as an impact mill, sugar grinders, spices and seasoning grinding pulverizers, an airflow jet pulverizer mill, and the like, the equipment selected according to the input slurry/suspension product, the drying process employed, and the physical properties of the dried output. The ultimate output product after grinding/pulverizing is a CBD/THC-containing salt, sugar, herb, spice, flavoring, additive, or the like, ready for use and consumption, with the CBD/THC accurately and reliably distributed.

As will be appreciated from the foregoing, in each of the embodiments above, the method of the present invention produces a cannabinoid-containing nanoparticle carrier composition that may be incorporated or used in particulate foods or food additives via a drum drying method.

BRIEF DESCRIPTION OF SEVERAL VIEWS OF THE DRAWINGS

Not applicable. The present invention, both as a process and as a product by process, may be understood without reference to illustrations.

DETAILED DESCRIPTION OF THE INVENTION

The inventive is first directed to a method of producing a cannabinoid nanoparticle carrier composition for therapeutic use, wherein the cannabinoid carrier composition improves bioavailabilty of the cannabinoids in the composition, as well as improves accurate dosing, due to the more precise measure. Various means of administration may be employed, including intraoral administration, peroral administration, transdermal administration, or intranasal administration. An exemplary composition produced by the inventive method may contain: (1) firstly, 1-15% Cannabinoids: Comprising of at least one of the Phytocannabinoids found in cannabis that include delta-9-Tetrahydrocannabinol (THC), Cannabidiol (CBD), Cannabinol (CBN) Cannabigerol (CBG}, Cannabigerol {CBG), Cannabichromene (CBC), Cannabicyclol (CBL), Canabivarol (CBV), Tetrahydrocannabiverin (THCV), Cannabidivarin (CBDV), Cannabichromevarin (CBCV, Cannabigerol Monoethyi ether (CBGM); (2) secondly, 1-20% Lipids (medium chain triglycerides, glycerides, hemps seed oil, safflower oil, sunflower oil, olive oil, etc.); and (3) thirdly, 1-10% pharmaceutical food grade surfactants (SpanLipophilic), (Tween-hydrophilic, e.g, as Tween 80, E433), to function as emulsifiers. They may be used independently or in any combination of the following: 20, sorbitan monopalmitate; Span® 40, sorbitan monopalmitate; Span® 60, sorbitan monostearate; and Span 80, sorbitan monooleate). Tween® are hydrophilic, Span® are lipophilic. [TWEEN is a registered trademark of Croda Americas LLC of Bridgewater, New Jersey; SPAN is a registered trademark of Merck KGaA of Darmstadt, Germany.]

An exemplary non-limiting method of making the inventive composition entails the following steps, wherein the steps are non-limiting in the relative proportions of the composition components and recited amounts are understood to be close approximations:

(1) Mixing 5000 mg of non-ionic surfactants with 9000 mg of cannabinoid oils, and 9000 mg lipids in a mixing vessel, e.g., a 200 ml beaker.

(2) Inducing sonication for 90 seconds at 60% amplification with a ultrasonic liquid processor until completely integrated.

(3) Dissolving 1000 mg of ascorbic acid into a carrier fluid selected from the group consisting of distilled water, glycerides, lipids, or a mixture thereof.

(4) Combining in sequence the non-ionic surfactants, lipids, and cannabanoid oil complex (COC) with the carrier fluid/ascorbic acid solution, which may consist of 76 g distilled water and 1000 mg ascorbic acid.

(5) Sonicating at 60% using ultrasonic liquid processor at 60% amplitude for 5 minutes, at a constant 24c temperature. The final weight of this exemplary nanoemulsion is 11.0 g at 100 ml.

The following protocol applies: The ingredients are processed using a single or dual phase process utilizing sonication or ultrasonic processes for a determined period of time to produce a water-soluble nanoemulsion.

The formula consists of: (a) non-ionic TWEEN® or SPAN® pharmaceutical food grade surfactants in specific combination or percentages to acquire 1-10% total surfactants; (b) refined olive oil 1 to 20%; (c) ascorbic acid 0.01-3%; (d) THC or CBD cannabinoids in any form of hemp or any classification form in any combination, whether concentration quantity or potency, 1-15%, in specific combinations; and (e) to achieve 100% of total formula weight or volume, the remaining ingredient is distilled water alone.

Importantly, the inventive composition does not include lecithin or lecithin-based essential phospholipids. Rather, it involves the use of sonication or ultrasonic processing of the water-immiscible mixture to achieve the nanoemulsion.

Next, the inventive process includes means of combining the cannabinoid nanoparticle carrier composition with any of a number of particulate food products, food additives, herbs and spices, flavorings, seasonings, salts, sugars, and monosodium glutamate.

Approximately 50 grams of a particulate herb, spice, flavoring, salt, sugar, preservative, or the like, are combined with 10 grams of a stable CBD/THC concentrate/emulsification made by the process set out, above. The ingredients are combined and blended to make a slurry or suspension, and the slurry or suspension is evaporated or dried to a solid state using an industrial food production drying process, spray drying, drum drying, vacuum band drying, tray drying, tunnel drying, and so on. The preferred process is spray or drum drying.

The dried product is then ground or pulverized to a nominal particle mass size using salt or sugar particle size as a datum reference. The resulting product is a CBD/THC particulate food product, food additive, herb, spice, salt, sugar, or preservative.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the claims included herein.

What is claimed as invention is:

1. A method of incorporating a cannabinoid nanoparticle carrier composition in particular foods and food additives, comprising:
    (a) mixing non-ionic surfactants with cannabinoid oils and lipids in a mixing vessel wherein the non-ionic surfactants, cannabinoid oils, and lipids, respectively, are mixed in proportions of 5.9:9 by weight of a total formula weight of the cannabinoid nanoparticle carrier composition;
    (b) processing the mixture made in step (a) using sonication for a predetermined time at a predetermined amplification until completely processed and substantially all of the cannabinoid oils are reduced to nanoparticle size in a cannabinoid oil complex (COC);
    (c) dissolving ascorbic acid in a carrier fluid to make an acidic carrier fluid solution, wherein the ascorbic acid is in a relative amount of 0.01-3% by weight of the total formula weight of the cannabinoid nanoparticle carrier composition;
    (d) mixing the COC made in steps (a) and (b) with the acidic carrier fluid solution made in step (c);
    (e) sonicating the mixture made in step (d) using an ultrasonic liquid processor operated at a predetermined amplitude for a predetermined time at a controlled temperature until substantially all of the cannabinoid oils in step (d) are returned to nanoparticle size to complete the process of making the cannabinoid nanoparticle carrier composition;
    (f) combining the cannabinoid nanoparticle carrier composition with a consumable particulate food product or food additive selected from the group consisting of herbs and spices, flavorings, seasonings, salts, sugars, and particular food preservatives, or any combination thereof;
    (g) blending the combination made in step (f) to make a slurry or suspension;
    (h) drying the slurry or suspension is evaporated or dried to a solid state; and
    (i) reducing the dried product to a nominal particle mass size suitable for human consumption.

2. The method of claim 1, wherein approximately 5 grams of a particulate herb, spice, flavoring, salt, sugar, preservative, or the like, are combined with 1 gram of a stable cannabinoid nanoparticle carrier composition.

3. The method of claim 1, wherein the drying step (h) is completed using an industrial food production drying process, spray drying, drum drying, vacuum band drying, tray drying, or tunnel drying.

4. The method of claim 1, wherein step (i) includes grinding pulverizing the dried product from step (h).

5. The method of claim 1, wherein step (i) includes using salt or sugar particle size as a datum reference.

6. The method of claim 1, wherein said step (a) mixing step comprises mixing approximately 5000 mg of non-ionic surfactants with approximately 9000 mg of cannabinoid oils, and approximately 9000 mg lipids.

7. The method of claim 1, wherein said step (b) processing step comprises inducing sonication for approximately 90 seconds at 60% amplification.

8. The method of claim 7, wherein said step (b) processing step involves using an ultrasonic liquid processor.

9. The method of claim 1, wherein said step (c) comprises dissolving approximately 1000 mg of ascorbic acid into a carrier fluid to make an acidic carrier fluid solution.

10. The method of claim 9, wherein said carrier fluid is selected from the group consisting of distilled water, glycerides, and lipids, and mixtures thereof.

11. The method of claim 10, wherein the acidic carrier fluid solution comprises approximately 76 g distilled water and 1 g (1000 mg) ascorbic acid.

12. The method of claim 11, wherein step (e) involves sonicating at 60% using ultrasonic liquid processor.

13. The method of claim 12, wherein the sonication of step (e) is conducted at 60% amplitude.

14. The method of claim 13, wherein the sonication of step (e) is continued for approximately 5 minutes.

15. The method of claim 14, wherein the sonication is carried out at a constant 24° C. temperature.

* * * * *